United States Patent [19]

Martell et al.

[11] Patent Number: 5,777,208

[45] Date of Patent: Jul. 7, 1998

[54] GAS SENSOR WITH PRESSURIZED SEAL

[75] Inventors: Dennis Martell, Naperville, Ill.; Richard Grove Warburton, Coraopolis, Pa.; Laura Ann Lindner, Oakdale, Pa.; Juergen Lindner, Bethel Park, Pa.

[73] Assignees: J and N Associates, Inc., Valparaiso, Ind.; National Draeger Incorporated, Pittsburgh, Pa.

[21] Appl. No.: 734,899

[22] Filed: Oct. 22, 1996

Related U.S. Application Data

[62] Division of Ser. No. 515,688, Aug. 16, 1995, Pat. No. 5,744,697.

[51] Int. Cl.[6] ..................................... G01N 27/26
[52] U.S. Cl. .................... 73/31.06; 73/31.05; 204/412; 204/414; 204/431
[58] Field of Search ................. 73/23.31, 31.05, 73/31.06; 204/412, 414, 431

[56] References Cited

U.S. PATENT DOCUMENTS

| | | | |
|---|---|---|---|
| 3,622,488 | 11/1971 | Chand et al. | 204/415 |
| 3,776,832 | 12/1973 | Oswin et al. | |
| 3,878,080 | 4/1975 | Luck . | |
| 3,909,386 | 9/1975 | Oswin et al. | |
| 4,036,724 | 7/1977 | Binder et al. | |
| 4,171,253 | 10/1979 | Nolan et al. | |
| 4,329,214 | 5/1982 | Spritzer et al. | |
| 4,478,704 | 10/1984 | Miyoshi et al. | |
| 4,525,266 | 6/1985 | Schmidt et al. | 204/412 |
| 4,621,035 | 11/1986 | Bruder . | |
| 4,688,021 | 8/1987 | Buck et al. | |
| 4,695,361 | 9/1987 | Grady . | |
| 4,717,633 | 1/1988 | Hauser . | |
| 4,767,994 | 8/1988 | Hopkins et al. | |
| 4,816,355 | 3/1989 | Kulibert et al. | |
| 4,874,500 | 10/1989 | Madou et al. | 204/412 |
| 4,900,643 | 2/1990 | Eskra et al. | |
| 4,948,681 | 8/1990 | Zagrodnik et al. | |
| 5,126,035 | 6/1992 | Kiesele et al. | 204/415 |
| 5,173,166 | 12/1992 | Tomantschger et al. | 204/412 |
| 5,250,171 | 10/1993 | Warburton et al. | 204/431 |
| 5,281,324 | 1/1994 | Kiesele et al. | 204/415 |
| 5,302,274 | 4/1994 | Tomantschger et al. | 204/412 |
| 5,314,605 | 5/1994 | Matthiessen | 204/415 |
| 5,331,310 | 7/1994 | Stetter et al. | |
| 5,336,390 | 8/1994 | Busack et al. | 204/431 |

FOREIGN PATENT DOCUMENTS

| | | |
|---|---|---|
| 0298570 | 1/1989 | European Pat. Off. . |
| 4025635 | 2/1991 | Germany . |

OTHER PUBLICATIONS

Blurton et al., "Controlled-potential electrochemical analysis of carbon monoxide", American Laboratory Jul. 1974, 5 pages.

Bay et al., "Electrochemical Technique for the Measurement of Carbon Monoxide", Analytical Chemistry, vol. 46, Oct. 1974, pp. 1837–1839.

Japanese Patent Abstract No. 62218852, dated Sep. 26, 1987.

Japanese Patent Abstract No. 4134234, dated May 8, 1992.

*Primary Examiner*—Hezron E. Williams
*Assistant Examiner*—Daniel S. Larkin
*Attorney, Agent, or Firm*—Marshall, O'Toole, Gerstein, Murray & Borun

[57] ABSTRACT

A gas sensor assembly having a first housing portion having a receptacle formed therein and a second housing portion in the form of a cover. A gas-sensing agent is disposed in the receptacle, and a working electrode, a counter electrode, and a reference electrode provided on a single electrode support sheet are disposed in fluid contact with the gas-sensing agent. The first housing portion is provided with three conductive housing portions which are in electrical contact with the three electrodes, and the cover maintains pressurized contact between the three conductive housing portions and the three corresponding electrodes. The gas sensor may be provided with two different types of leakage detectors to sense leakage of the gas-sensing agent from the sensor.

6 Claims, 2 Drawing Sheets

GAS SENSOR WITH PRESSURIZED SEAL

This is a Divisional of U.S. application Ser. No. 08/515,688, filed Aug. 16, 1995 now U.S. Pat. No. 5,744,699.

BACKGROUND OF THE INVENTION

The present invention is directed to a gas sensor used to detect the presence of gases, such as carbon monoxide.

Most commercially available gas sensors are of the amperometric type having two or more electrodes in which a catalytically active metal is fixed to a porous substrate. The porous substrate operates as a gas permeable membrane. The electrodes are located on the inside surface of the membrane where they are immersed in an electrolyte such as sulfuric acid. External circuitry maintains one of the electrodes, the working electrode, at a given electrical potential with respect to one of the other electrodes.

When the gas of interest diffuses through the porous membrane to reach the working electrode, the diffused gas is oxidized or reduced at the interface of the working electrode and the electrolyte. That reaction generates an electrical current that is proportional to the concentration of the gas. In some cases, the gas of interest reacts with another chemical which, in turn, is oxidized or reduced. In some cases, sensors are of a galvanic design wherein a metal such as lead is oxidized to provide the potential at the working electrode.

In the prior art, the sensors were connected to the external circuit through wires. For example, a platinum contact wire was connected to the catalytically active electrode and passed through the sensor body to an external contact. Since most sensors contain a corrosive, liquid electrolyte, a difficulty with sensors has been providing secure electrical contact with the electrodes while maintaining a seal at the location where the conductor passes through the sensor body. In the prior art, seals around conductors have included Teflon gaskets. In other methods, the seal has been made of thermoplastic material or epoxy resin.

One difficulty with such prior art sensors has been that such seals were difficult and expensive to make. Accordingly, there was a need in the prior art for an improved sensor design that would avoid the need for such seals and thereby be more reliable and less expensive to manufacture. Also, there was a need for a sensor that was mechanically stronger and more durable than sensors known in the prior art wherein the electrodes were connected to platinum wires.

Previous carbon monoxide sensors are relatively complicated in design and suffer from a number of disadvantages due to the use of sulfuric acid, which is typically used as the electrolyte. These disadvantages include the fact that the sulfuric acid may leak from the sensor and/or cause the internal components of the sensor to corrode.

SUMMARY OF THE INVENTION

The present invention is directed to a gas sensor, such as a carbon monoxide sensor, which is relatively simple in structure and inexpensive to manufacture.

In one aspect, the invention is directed to a gas sensor assembly having a housing with a receptacle formed therein, a gas-sensing agent disposed in the receptacle, and a plurality of electrodes disposed in fluid contact with the gas-sensing agent. The housing has a plurality of conductive housing portions, each of which is conductively coupled to a respective one of the electrodes, and a non-conductive housing portion conductively separating the conductive housing portions. By providing the conductive housing portions instead of the relatively thin wires typically used to connect the gas sensor electrodes to a conventional gas sensing circuit, assembly of the gas sensor is simplified and a more rugged construction is obtained.

In another aspect, the invention is directed to a gas sensor assembly having a housing with a receptacle formed therein, a gas-sensing agent disposed in the receptacle, and a plurality of electrodes disposed in fluid contact with the gas-sensing agent. The gas sensor has a plurality of conductive members, one for each electrode, and means for maintaining pressurized contact between the conductive members and the electrodes. The means for maintaining pressurized contact, which preferably provides a pressure of at least about 20 pounds per square inch between the electrodes and the conductive members, may comprise a second housing portion, such as a cover, and a rubber gasket disposed between the housing portion and the second housing portion. The gas sensor may include a single electrode support sheet, disposed between the rubber gasket and the housing portion, having the electrodes formed thereon.

In a further aspect, the invention is directed to a gas sensor assembly having a housing with a receptacle formed therein, a gas-sensing agent disposed in the receptacle, a plurality of electrodes disposed in fluid contact with the gas-sensing agent, and a plurality of conductive members, each of which is disposed in electrical contact with a respective one of the electrodes. A closure member is disposed adjacent the housing in which the receptacle is formed, and a liquid-tight seal is formed between the closure member and the housing forming the receptacle so that the closure member and the housing form an enclosed liquid-tight chamber. None of the electrodes and none of the conductive members pass through the liquid-tight seal, thus ensuring that the integrity of the seal is not compromised. The closure member may comprise an electrode support sheet on which the electrodes are formed.

In another aspect, the invention is directed to a gas sensor assembly having a housing with a receptacle formed therein, a gas-sensing agent disposed in the receptacle, and a plurality of electrodes disposed in fluid contact with the gas-sensing agent. The gas sensor includes a leakage detector, disposed in the housing, which generates a visual indication of leakage upon the gas-sensing agent coming into contact with the leakage detector. The leakage detector may comprise a substantially flat sheet impregnated with a material which changes color upon coming into contact with the gas-sensing agent, and the flat sheet may be disposed directly beneath a transparent portion of the gas sensor housing so that the color change is readily apparent.

In another aspect, the invention is directed to a gas sensor assembly having a housing with a receptacle formed therein, a gas-sensing agent disposed in the receptacle, and a plurality of electrodes disposed in fluid contact with the gas-sensing agent. The gas sensor includes a leakage detector in the form of a pair of spaced conductive members associated with the housing, the spaced conductive members being provided adjacent the receptacle. The spaced conductive members have a relatively high resistance between them in the absence of gas-sensing agent coming into contact with them and a relatively low resistance between them in the presence of gas-sensing agent coming into contact with them. The change in resistance due to gas-sensing agent leaking from the receptacle and coming into contact with the spaced conductive members can be detected.

These and other features and advantages of the present invention will be apparent to those of ordinary skill in the art

DETAILED DESCRIPTION OF A PREFERRED EMBODIMENT

Figure 1:
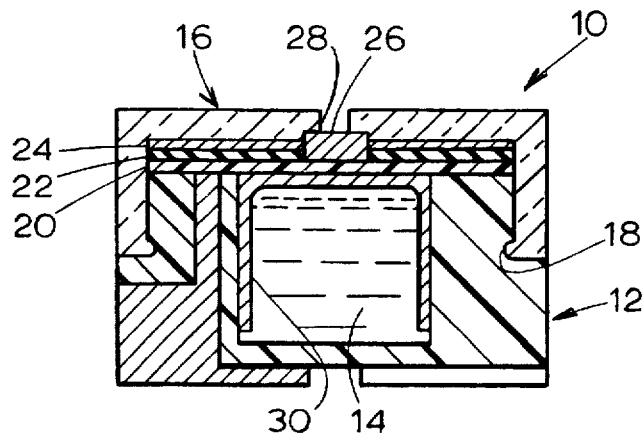
FIG. 1 is a cross-sectional view of a preferred embodiment of a gas sensor in accordance with the invention.

A preferred embodiment of an electrochemical sensor 10 in accordance with the invention is illustrated in FIG. 1. The sensor 10 has a housing composed of a first, generally cup-shaped housing portion 12 (see also FIG. 4) in which a receptacle 14 for the storage of an electrolyte or gas-sensing agent is formed and a second housing portion in the form of a snap-fit cover 16 which is retained on the cup-shaped housing portion 12 via an annular rib 18, integrally formed with the cover 16, which rests in a matching annular groove formed in the housing portion 12.

A flat circular electrode support element, in the form of a sheet 20, a rubber gasket 22, and a leakage detector in the form of a leakage-indicating sheet 24 are disposed between the housing portion 12 and the cover 16. The rubber gasket 22 and the sheet 24 are flat and circular and each have a central hole formed therein in which a small cylindrical filter 26 is disposed. The leakage-indicating sheet 24 may be composed of a paper-like substrate, such as Paper No. BSF-65 commercially available from Whatman Specialty Co., impregnated with a conventional agent, such as dimethyl yellow, which changes color (in this case to red) when the gas-sensing agent comes into contact with it. The change in color can be viewed through the cover 16, which is formed of a transparent material.

The cover 16 has an opening or sensing hole 28 formed therein directly above the filter 26 so as to expose the filter 26 to the ambient atmosphere to be sensed by the gas sensor 10. The purpose of the filter 26, which may be a rubber charcoal filter, is to prevent certain gases (which are not to be sensed) that may interfere with the sensing of the desired gas(es) from passing into the interior of the sensor 10 where the gas-sensing reaction takes place. The electrode support sheet 20 is hydrophobic to prevent the liquid gas-sensing agent from escaping from the sensor 10 via the sensing hole 28 but allows passage there through of the gaseous atmosphere to be sensed.

The gas sensor 10 includes a wick 30, which may be composed of glass paper, for example. The wick 30 includes a first portion, shown horizontally in FIG. 1, which abuts the underside of the electrode support sheet 20 and several portions which extend downwardly into the gas-sensing agent disposed in the receptacle 14. The purpose of the wick 30 is to maintain the underside of the electrode support sheet 20 (which has three electrodes formed thereon) in fluid contact with the gas-sensing agent. Where the gas sensor 10 is used to detect the presence of carbon monoxide, the gas-sensing agent may be a 30% sulfuric acid gel.

Figure 3:
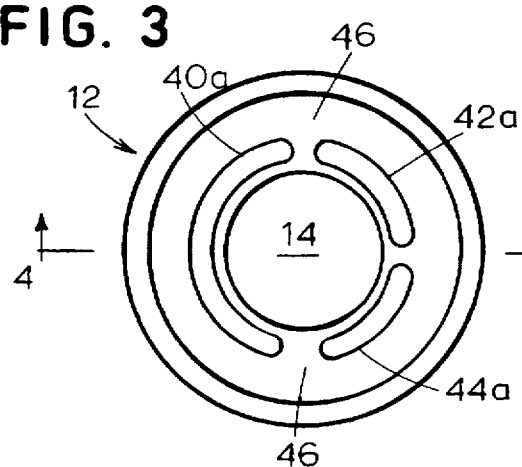
FIGS. 3–6 are various views of a housing portion of the sensor of FIG. 1 in which a receptacle for the storage of a gas-sensing agent is formed.
Figure 4:
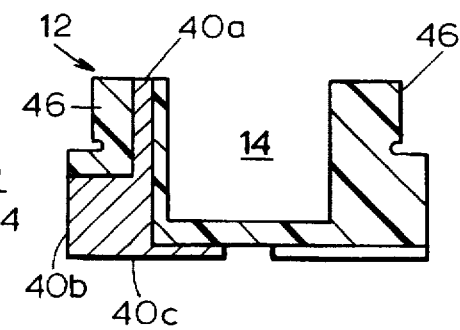
Figure 5:
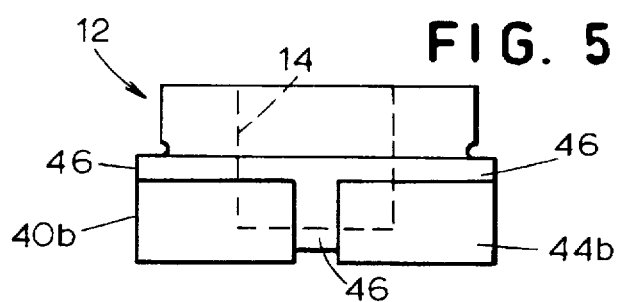
Figure 6:
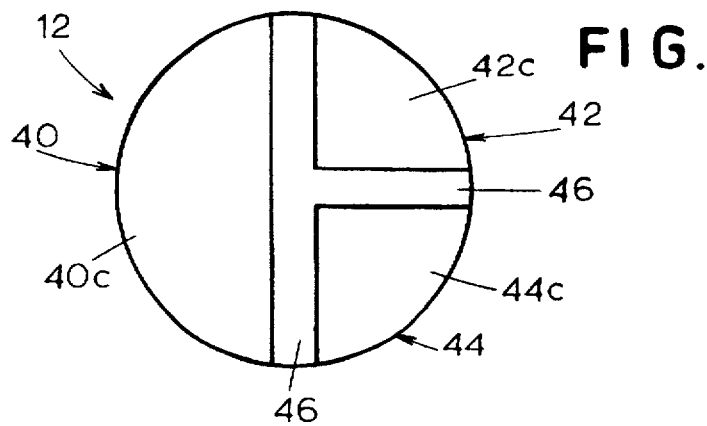

FIG. 3 is a top view of the cup-shaped housing portion 12 having the receptacle 14 formed therein. The cup-shaped housing 12 has three conductive housing portions 40, 42, 44, each of which serves as an electrical conductor. The three conductive portions 40, 42, 44 are electrically isolated from each other by the remaining non-conductive portions 46 of the housing 12. The conductive portion 40 is composed of three portions: an arcuate upper portion 40a having a relatively small radial width, a side portion 40b having a relatively large radial width, and a bottom portion 40c, all three of which are shown in FIG. 4. The side portion 40b acts as a side contact surface at which an electrical connection can be made, and the bottom portion 40b acts as a bottom contact surface at which an electrical connection can be made. The shapes of the conductive portions 42, 44 are similar to that of the conductive portion 40 in that they each have an arcuate upper portion (e.g. portion 44a) having a relatively small radial width, a side portion (e.g. portion 44b) having a relatively large radial width, and a bottom portion (e.g. portion 44c).

It is not necessary that the conductive housing portions 40, 42, 44 have both side and bottom portions; the provision of both side and bottom portions simply increases the area to which electrical connection may be made. The shape of the conductive portions 40, 42, 44 may be varied from those shown in FIGS. 3–6.

Figure 2:
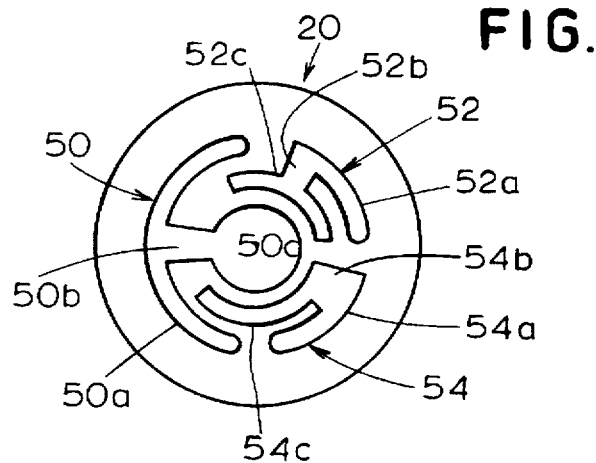
FIG. 2 is an illustration of an electrode support sheet used in the sensor of FIG. 1.

The electrode support sheet 20, the bottom surface of which is shown in FIG. 2, has three conductive electrode patterns 50, 52, 54 formed thereon. The pattern 50, which acts as a working electrode, includes a first central portion 50c, a second portion 50a, and a third portion 50b which electrically interconnects the portions 50a, 50c. The pattern 52, which acts as a reference electrode, and the pattern 54, which acts as a counter electrode, are similarly composed of three conductive portions 52a, 52b, 54a, 54b, 54c. The electrode patterns 50, 52, 54 may comprise platinum powder disposed on a Teflon substrate in a conventional manner.

When the electrode support sheet 20 is placed on top of the housing portion 12, the conductive portions 50a, 52a, 54a of the electrode support sheet 20 are aligned and make contact with the arcuate conductive portions 40a, 42a, 44a of the housing 12. The electrode support sheet 20 may be provided with an alignment mechanism, such as a tab (not shown), to ensure that the conductive portions 50a, 52a, 54a are accurately aligned with the conductive portions 40a, 42a, 44a.

In the manufacture of the gas sensor 10, the cup-shaped housing 12 is formed via a conventional dual-injection molding process described as follows. First, the housing 12 without the three conductive portions 40, 42, 44 is injection-molded in a first mold with a non-conductive plastic, such as polypropylene. The result of the first mold will be a housing portion 12 as shown in FIGS. 3–6, but with air being present where the conductive portions 40, 42, 44 are shown. The housing portion 12 is then placed in a second mold, and the conductive portions 40, 42, 44 are injection-molded with a conductive plastic, such as polypropylene having carbon or other conductive fragments melted therein. The result of this conventional dual-molding process is the housing 12 shown in FIGS. 3–6 in which the non-conductive portions 46 and the conductive portions 40, 42, 44 together form a unitary construction.

Figure 7A:
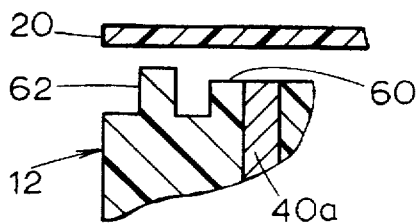
FIGS. 7A and 7B illustrate the formation of a heat seal utilized in the sensor of FIG. 1.
Figure 7B:
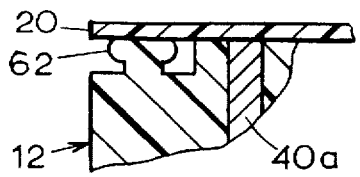

After the cup-shaped housing 12 is formed, a suitable gas-sensing agent is disposed within the receptacle 14, and then the wick 30 is disposed over the gas-sensing agent. The receptacle 14 is then sealed via a heat-sealing process to give it a liquid-tight seal. Referring to FIG. 7A, a portion of the sidewall of the cup-shaped housing 12 and a portion of the electrode support sheet 20 are shown enlarged. The cup-shaped housing 12 has an upper surface 60 and a meltable member 62 having an upper surface which is at a greater elevation than the surface 60. During the heat-sealing process, the electrode support sheet 20 is forced downwards over the top of the cup-shaped housing 12 by a flat heated platen (e.g. 210° C.) for a predetermined period of time (e.g. five seconds). As a result, the meltable member 62 will melt, as shown in FIG. 7B, to form a heat-sealed bond with the electrode support sheet 20. It should be understood that since the overall shape of the meltable member 62 is circular and since the circular member 62 surrounds the entire outer periphery of the cup-shaped housing 12, a heat-sealed bond is formed about the entire periphery of the housing 12 so that the gas-sensing agent is completely confined within the receptacle 14.

To facilitate ease of manufacture, the gas-sensing agent may be introduced into the housing 12, after the heat seal is formed as described above, through a hole or tube in the bottom of the housing 12 (with the housing 12 being inverted). After the gas-sensing agent is added, the hole or tube is permanently closed (e.g. in the case of a meltable tube, by melting the tube closed).

One advantage of the manner of making the heat seal described above is that the Teflon material of the electrode support element 20 is bonded directly to the polypropylene plastic of the cup-shaped housing 12, with no conductive portions 40, 42, 44 or 50, 52, 54 coming into contact with the seal. That is advantageous because the heat-sealing of Teflon and polypropylene forms a relatively strong bond, while the presence of conductive portions, such as those formed by platinum powder, may result in a weaker bond.

After the heat-sealed bond is formed, the rubber gasket 22, the leakage-indicating sheet 24, and the filter 26 are placed on the electrode support sheet 20, and the cover 16 is snap-fit over the assembly and is retained in place by the annular rib 18. The vertical location of the rib 18 with respect to the underside of the cover 16 is dimensioned so that, when the cover 16 snap-fit onto the housing portion 12, the underside of the cover 16 exerts a pressure of at least about 20 psi, and preferably about 25 psi, on the electrode support sheet 20, thus ensuring that the conductive portions 50a, 52a, 54a of the electrode support sheet 20 are always in electrical contact with the conductive portions 40a, 42a, 44a of the housing 12.

In operation, to detect a gas, a constant voltage is placed between the working electrode 50c and the reference electrode 52c via the conductive contact portions 40c and 42c (which are electrically connected to the electrodes 50c, 52c, respectively). Then, upon the presence of the gas being detected through the sensing hole 28, an electrical current will be induced between the working electrode 50c and the counter electrode 54c, which current can be detected and measured by a conventional current sensing circuit attached to the conductive contact portions 40c and 44c (which are electrically connected to the electrodes 50c and 54c).

Figure 8:
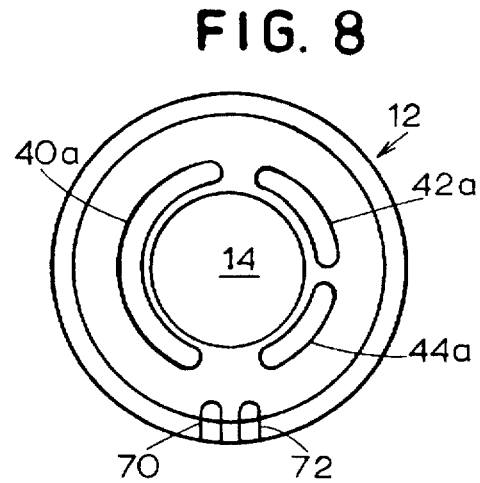
FIGS. 8 and 9 illustrate an alternative embodiment of a gas sensor in accordance with the invention.
Figure 9:
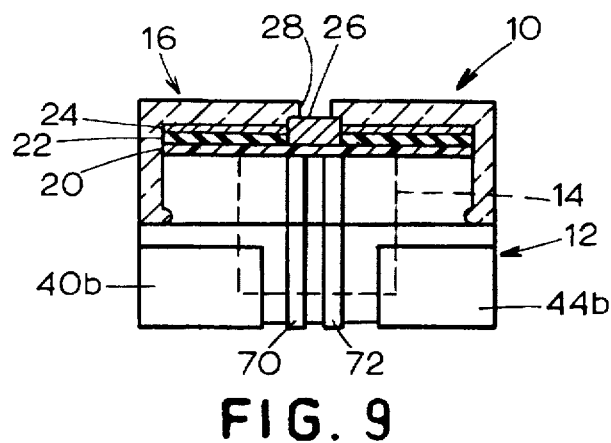

A second embodiment of the gas sensor 10 is illustrated in FIGS. 8 and 9. Referring to those figures, the cup-shaped housing 12 is modified by the addition of two conductive housing portions 70, 72 which together act as a second type of leakage detector. In the event that any gas-sensing agent leaks from the receptacle 14 and bridges the gap between the two conductive housing portions 70, 72, the electrical resistance between those two portions 70, 72 will change from a relatively large value (due to the non-conductive housing portion separating the portions 70, 72) to a relatively small value (since the gas-sensing agent has a relatively low electrical resistance). This significant change in resistance can be detected in a conventional manner by a conventional detecting circuit connected to both of the conductive portions 70, 72. The conductive portions 70, 72 are formed in the same manner as the conductive portions 40, 42, 44 formed during the dual-injection molding process described above.

Additional modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A gas sensor assembly comprising:

a first housing portion having a receptacle formed therein;

a gas-sensing agent disposed in said receptacle;

a plurality of electrodes disposed in fluid contact with said gas-sensing agent;

a plurality of conductive members, each of said conductive members being associated with a respective one of said electrodes;

a second housing portion;

a sealing member disposed between said first housing portion and said second housing portion; and an electrode support sheet disposed between said sealing member and said receptacle, said electrodes being formed on said electrode support sheet.

2. A gas sensor assembly as defined in claim 1 wherein said housing portions and said sealing member are adapted to maintain at least about 20 pounds per square inch of pressure between said conductive members and said electrodes.

3. A gas sensor assembly as defined in claim 1 wherein each of said conductive members comprises a conductive portion of said housing.

4. A gas sensor assembly comprising:

a housing portion having a receptacle formed therein;

a gas-sensing agent disposed in said receptacle;

a plurality of electrodes disposed in fluid contact with said gas-sensing agent;

a plurality of conductive members, each of said conductive members being associated with a respective one of said electrodes; and means for maintaining pressurized contact between said conductive members and said electrodes wherein said means for maintaining pressurized contact comprises a second housing portion and a rubber gasket disposed between said housing portion and said second housing portion, said gas sensor assembly additionally comprising an electrode support sheet disposed between said rubber gasket and said receptacle, said electrodes being formed on said electrode support sheet.

5. A gas sensor assembly as defined in claim 4 wherein said means for maintaining pressurized contact comprises means for maintaining at least about 20 pounds per square inch of pressure between said conductive members and said electrodes.

6. A gas sensor assembly as defined in claim 4 wherein each of said conductive members comprises a conductive portion of said housing.

* * * * *